(12) United States Patent
Katsumoto

(10) Patent No.: US 10,295,524 B2
(45) Date of Patent: May 21, 2019

(54) ELECTRICAL MEASURING CARTRIDGE, AS WELL AS ELECTRICAL MEASURING APPARATUS AND ELECTRICAL MEASURING METHOD

(71) Applicant: Sony Corporation, Tokyo (JP)

(72) Inventor: Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 206 days.

(21) Appl. No.: 14/628,550

(22) Filed: Feb. 23, 2015

(65) Prior Publication Data

US 2015/0253269 A1    Sep. 10, 2015

(30) Foreign Application Priority Data

Mar. 4, 2014    (JP) .................... 2014-041915

(51) Int. Cl.
| | |
|---|---|
| *B01L 3/00* | (2006.01) |
| *G01N 27/07* | (2006.01) |
| *G01N 33/483* | (2006.01) |
| *G01N 33/487* | (2006.01) |

(52) U.S. Cl.
CPC .......... *G01N 33/483* (2013.01); *B01L 3/5085* (2013.01); *G01N 27/07* (2013.01); *G01N 33/48707* (2013.01); *B01L 2300/0645* (2013.01)

(58) Field of Classification Search
CPC .......... G01N 33/483; G01N 33/48707; G01N 27/07; B01L 3/5085; B01L 2300/0645
See application file for complete search history.

(56) References Cited

U.S. PATENT DOCUMENTS

| | | | |
|---|---|---|---|
| 5,186,800 A | 2/1993 | Dower | |
| 2006/0160205 A1* | 7/2006 | Blackburn | B01F 13/0059 435/287.2 |
| 2007/0217956 A1* | 9/2007 | Pamula | B01F 13/0071 422/400 |
| 2008/0221805 A1* | 9/2008 | Andrews | G01N 15/1031 702/19 |
| 2011/0079521 A1* | 4/2011 | Revol-Cavalier | A61B 5/4266 205/789 |
| 2016/0327504 A1 | 11/2016 | Katsumoto | |

FOREIGN PATENT DOCUMENTS

| | | |
|---|---|---|
| JP | 2009-042141 A | 2/2009 |
| JP | 2010-181400 A | 8/2010 |
| JP | 2012-052906 A | 3/2012 |

* cited by examiner

*Primary Examiner* — Robert J Eom
(74) *Attorney, Agent, or Firm* — Wolf, Greenfield & Sacks, P.C.

(57) ABSTRACT

There is provided an electrical measuring cartridge of a biological sample, the electrical measuring cartridge including at least a plurality of biological sample holding sections each being configured to contain the biological sample, and a pair of electrical conductive sections fixed to each of the biological sample holding sections.

13 Claims, 14 Drawing Sheets

1: ELECTRICAL MEASURING CARTRIDGE
11: BIOLOGICAL SAMPLE HOLDING SECTION
12: ELECTRICAL CONDUCTIVE SECTION
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
13: CLOSING UNIT
R: REAGENT

1: ELECTRICAL MEASURING CARTRIDGE
11: BIOLOGICAL SAMPLE HOLDING SECTION
12: ELECTRICAL CONDUCTIVE SECTION

1: ELECTRICAL MEASURING CARTRIDGE
11: BIOLOGICAL SAMPLE HOLDING SECTION
12: ELECTRICAL CONDUCTIVE SECTION
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION

1: ELECTRICAL MEASURING CARTRIDGE
11: BIOLOGICAL SAMPLE HOLDING SECTION
12: ELECTRICAL CONDUCTIVE SECTION
122a: COMMON ELECTRODE
122b: ELECTRODE SECTION TO BE PAIRED WITH COMMON ELECTRODE
123a: CONNECTION SECTION LINKED TO 122a
123b: CONNECTION SECTION LINKED TO 122b

1: ELECTRICAL MEASURING CARTRIDGE
11: BIOLOGICAL SAMPLE HOLDING SECTION
12: ELECTRICAL CONDUCTIVE SECTION
122: ELECTRODE SECTION
123: CONNECTION SECTION
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
122: ELECTRODE SECTION
123: CONNECTION SECTION
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
122a: COMMON ELECTRODE
122b: ELECTRODE SECTION TO BE PAIRED WITH COMMON ELECTRODE
123a: CONNECTION SECTION LINKED TO 122a
123b: CONNECTION SECTION LINKED TO 122b
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
122a: COMMON ELECTRODE
122b: ELECTRODE SECTION TO BE PAIRED WITH COMMON ELECTRODE
123a: CONNECTION SECTION LINKED TO 122a
123b: CONNECTION SECTION LINKED TO 122b
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
122a: COMMON ELECTRODE
123a: CONNECTION SECTION LINKED TO 122a
S: BIOLOGICAL SAMPLE

1: ELECTRICAL MEASURING CARTRIDGE
11: BIOLOGICAL SAMPLE HOLDING SECTION
12: ELECTRICAL CONDUCTIVE SECTION
2: CARTRIDGE INSERTION SECTION
3: APPLICATION UNIT
4: MEASUREMENT UNIT
S: BIOLOGICAL SAMPLE
10: ELECTRICAL MEASURING APPARATUS

1: ELECTRICAL MEASURING CARTRIDGE
11: BIOLOGICAL SAMPLE HOLDING SECTION
12: ELECTRICAL CONDUCTIVE SECTION
2: CARTRIDGE INSERTION SECTION
3: APPLICATION UNIT
4: MEASUREMENT UNIT
S: BIOLOGICAL SAMPLE
10: ELECTRICAL MEASURING APPARATUS

1: ELECTRICAL MEASURING CARTRIDGE
11: BIOLOGICAL SAMPLE HOLDING SECTION
12: ELECTRICAL CONDUCTIVE SECTION
S: BIOLOGICAL SAMPLE
K: ELECTRICAL MEASURING KIT
5: BIOLOGICAL SAMPLE INTRODUCING MEMBER
51: TIP HAVING PIPETTE SHAPE

ELECTRICAL MEASURING CARTRIDGE, AS WELL AS ELECTRICAL MEASURING APPARATUS AND ELECTRICAL MEASURING METHOD

CROSS REFERENCE TO RELATED APPLICATIONS

This application claims the benefit of Japanese Priority Patent Application JP 2014-041915 filed Mar. 4, 2014, the entire contents of which are incorporated herein by reference.

BACKGROUND

The present technology relates to an electrical measuring cartridge for measuring electrical properties of a biological sample. More particularly, the present technology relates to an electrical measuring cartridge of a biological sample, in which the electrical measuring cartridge enables a plurality of electrical measurements to be performed simply and at high accuracy. The present technology also relates to an electrical measuring apparatus and an electrical measuring method using the electrical measuring cartridge.

Measurement of electrical properties of a biological sample, determination of physical properties of the biological sample from the measurement result, and discrimination of a kind of cell or the like included in the biological sample, and so on, are performed (for example, see Japanese Patent Application Laid-open No. 2009-042141). The measured electrical properties may be complex permittivity or frequency dispersion (a dielectric spectrum) thereof. The complex permittivity or the frequency dispersion is generally calculated by measuring a complex capacitance and complex impedance between electrodes using a solution retainer or the like including the electrodes configured to apply a voltage to a solution.

In addition, for example, in Japanese Patent Application Laid-open No. 2010-181400, a technology of obtaining information related to blood coagulation from permittivity of blood is disclosed, and "a blood coagulation system analysis device including a pair of electrodes, an application unit configured to apply an alternating current voltage to the pair of electrodes at predetermined time intervals, a measurement unit configured to measure the permittivity of the blood disposed between the pair of electrodes, and an analysis unit configured to analyze a level of function of the blood coagulation system using the permittivity of the blood measured at the time intervals after an action of the anticoagulant agent functioned in the blood is released" is disclosed.

When the electrical properties of the biological sample are measured, as a container configured to accommodate the biological sample, for example, Japanese Patent Application Laid-open No. 2012-052906 discloses a sample cartridge having a cylindrical body made of an insulating material, configured to hold the biological sample in a region including surfaces of electrodes inserted into an inner hole from both of end openings and a surface of the inner hole, and in which a constriction section disposed between the two opposite electrodes and formed by constricting the inner hole is installed at that region, measuring electrical properties of a biological sample.

Here, when measuring electrical properties of a biological sample, a plurality of measurements is performed in many cases, and determination is made in a comprehensive manner from the obtained plurality of measurement results.

However, the sample cartridge that measures electrical properties of a biological sample disclosed in Japanese Patent Application Laid-open No. 2012-052906 has only one region where a biological sample can be held. Therefore, the sample cartridge in the conventional form comes to be necessary for each measurement when performing a plurality of measurements, and thus has not matched practical situations when measuring electrical properties.

SUMMARY

Since the electrical measuring cartridge in the conventional form comes to be necessary for each measurement when performing a plurality of measurements, there has been a problem that handling and data management of a biological sample for each measurement become complicated, and a measurement mechanism of the electrical measuring apparatus becomes complicated.

To address this concern, it is desirable to provide an electrical measuring cartridge of a biological sample, in which the electrical measuring cartridge enables a plurality of electrical measurements to be performed simply and at high accuracy.

The inventors of the present application have intensively conducted research on a structure of a cartridge used when measuring electrical properties of a biological sample. As a result, the inventors have achieved the present technology by devising a structure in which a plurality of regions each being capable of holding a biological sample is provided within one cartridge.

According to an embodiment of the present disclosure, there is provided an electrical measuring cartridge of a biological sample, the electrical measuring cartridge including at least a plurality of biological sample holding sections each being configured to contain the biological sample, and a pair of electrical conductive sections fixed to each of the biological sample holding sections.

According to the electrical measuring cartridge, the biological sample holding sections and the electrical conductive sections may be integrally molded in a state where the electrical conductive sections are partly embedded in the biological sample holding sections.

The biological sample holding sections may be made of resin.

The electrical conductive sections may be insert molded and integrated to the biological sample holding sections.

The respective electrical conductive sections fixed to the at least two or more biological sample holding sections may be aligned along an identical plane of the cartridge.

The respective electrical conductive sections fixed to the at least two or more biological sample holding sections are molded by being molded in a state of having linkage sections to which portions of the electrical conductive sections are linked, and then cutting off the linkage sections.

The cutting-off may be performed after the electrical conductive sections are integrally molded to the biological sample holding sections although a time to cut off the linkage sections is not especially limited.

Each of the electrical conductive sections may include at least an electrode section that comes into contact with the biological sample during measurement, and a connection section configured to electrically connect to an external circuit.

The electrode sections may be partly used as a common electrode.

A reagent may be enclosed in a part of the biological sample holding sections.

The biological sample is not especially limited, but may be liquid.

The biological sample may contain a blood component.

The electrical measuring cartridge may be used as a part of an electrical measuring apparatus appropriately.

Specifically, according to an embodiment of the present disclosure, there is provided the electrical measuring apparatus including at least: a cartridge insertion section into which an electrical measuring cartridge of a biological sample is inserted, the electrical measuring cartridge including at least a plurality of biological sample holding sections each being configured to contain the biological sample, and a pair of electrical conductive sections fixed to each of the biological sample holding sections; an application unit that applies a voltage to the electrical conductive sections; and a measurement unit that measures an electrical property of the sample.

Also, the electrical measuring cartridge according to an embodiment of the present technology can be preferably used in an electrical measuring method of measuring electrical properties of a biological sample.

The electrical measuring cartridge according to an embodiment of the present technology has a plurality of biological sample holding sections each configured to contain a biological sample, and a pair of electrical conductive sections fixed to each of the biological sample holding sections, thereby enabling a plurality of electrical measurements to be performed simply and at high accuracy. It is noted that the effects described herein are not necessarily limited, and any one of the effects described in the present technology may be exerted.

DETAILED DESCRIPTION OF THE EMBODIMENT(S)

Figure 1A:
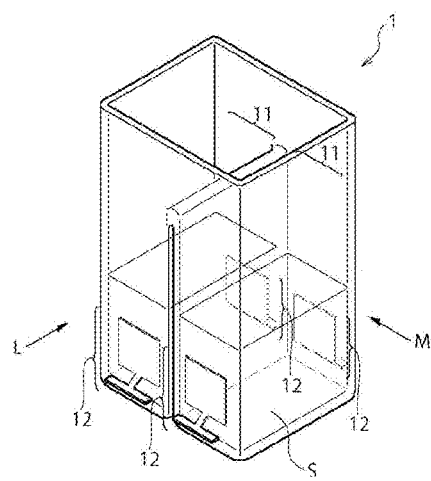
FIG. 1A is a schematic diagram schematically illustrating a first embodiment according to the present technology of an electrical measuring cartridge 1.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

It is noted that embodiments described below are examples of a representative embodiment of the present technology, and do not cause the scope of the present technology to be narrowly interpreted. It is noted that description will be provided in the following order.

1. Electrical measuring cartridge 1
  (1) Biological sample holding section 11
  (2) Electrical conductive section 12
    (a) Linkage section 121
    (b) Electrode section 122
    (c) Connection section 123
      <First Embodiment>
      <Second Embodiment>
      <Third Embodiment>
      <Fourth Embodiment>
      <Fifth Embodiment>
  (3) Biological sample S
  (4) Others 2. Electrical measuring apparatus 10
(1) Cartridge insertion section 2
(2) Application unit 3
(3) Measurement unit 4
(4) Others
3. Electrical measuring kit K
(1) Biological sample introducing member 5
4. Electrical measuring method

1. Electrical Measuring Cartridge 1

FIG. 1A is a schematic diagram schematically illustrating a first embodiment according to the present technology of an electrical measuring cartridge 1. The electrical measuring cartridge 1 according to the embodiment of the present technology is a cartridge used for holding a biological sample when measuring electrical properties of the biological sample. The electrical measuring cartridge 1 according to the embodiment of the present technology roughly includes at least a biological sample holding section 11 and an electrical conductive section 12. Hereinafter, each component will be described in detail. It is noted that although a biological sample S or a reagent R is illustrated for descriptive purposes in the drawings, the biological sample S or the reagent R is not included in the electrical measuring cartridge 1 according to the embodiment of the present technology.

(1) Biological Sample Holding Section 11

In the electrical measuring cartridge 1 according to the embodiment of the present technology, the biological sample holding section 11 is a site used for holding a biological sample S to be measured. Also, the electrical measuring cartridge 1 according to the embodiment of the present technology includes a plurality of biological sample holding sections 11. It is noted that "a plurality of" means at least two or more.

Since the electrical measuring cartridge 1 according to the embodiment of the present technology includes the plurality of biological sample holding sections 11, a plurality of measurement results can be obtained with one electrical measuring cartridge 1. Therefore, handling and data management of a plurality of biological samples S become easy, reducing human error such as a mix-up of the biological samples S. As a result, there is achieved the improvement of user's convenience and measurement accuracy when measuring electrical properties.

Also, the use of the electrical measuring cartridge 1 according to the embodiment of the present technology facilitates mechanical switchover for each measurement on an electrical measuring apparatus side, resulting in a simple measurement mechanism for the apparatus to be realized. Furthermore, a cost of the apparatus itself decreases, while a plurality of electrical measurements can be performed at high accuracy.

When the electrical properties of the biological sample S are measured, a set of a predetermined plurality of measurements is usually executed. For example, when the electrical properties of blood as the biological sample S are measured, a set of a plurality of measurements is executed for a prothrombin time, a partial thromboplastin time, a plasma thrombin time, and the like. Since the electrical measuring cartridge 1 according to the embodiment of the present technology can concurrently perform a plurality of electrical measurements, a cost for each measurement can be reduced when the plurality of measurements is considered as one set.

In the electrical measuring cartridge 1 according to the embodiment of the present technology, the form of the biological sample holding section 11 is not particularly limited, and can be freely designed depending on the type of the biological sample S, the measurement method, the electrical measuring apparatus to be used, and the like. Examples of the form may include a cylindrical body, a polygonal barrel having a polygonal cross section (triangle, square, or more), a circular cone, a polygonal cone having a polygonal cross section (triangle, square, or more), and one or a combination of two or more thereof.

In the present technology, the biological sample holding section 11 preferably has a form in which at least a portion on which the electrical conductive section 12 is disposed is planar. In general, an electrode used when measuring electrical properties often has a planer or plate-like form. In the biological sample holding section 11 according to the embodiment of the present technology, when the cylindrical shape is selected, the electrical conductive section 12 having a planer or plate-like shape comes to be attached to a curved portion, causing a manufacturing process to become extraordinarily complicated. Also, when the electrical conductive section 12 having a planer or plate-like shape is attached to the curved portion of the biological sample holding section 11, a step is likely to be generated at a connection portion between the biological sample holding section 11 and the electrical conductive section 12. Accordingly, measurement accuracy sometimes decreases when measuring electrical properties. Therefore, in the biological sample holding section 11, the simplification of a manufacturing process of the electrical measuring cartridge 1 and the improvement of measurement accuracy can be achieved by selecting the form in which at least a portion on which the electrical conductive section 12 is disposed is planer.

Figure 1B:
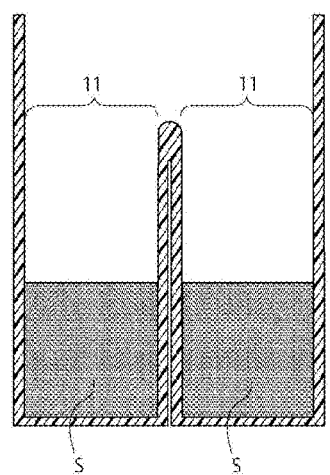
FIG. 1B is an arrow end view seen from the L side of FIG. 1A.
Figure 1C:
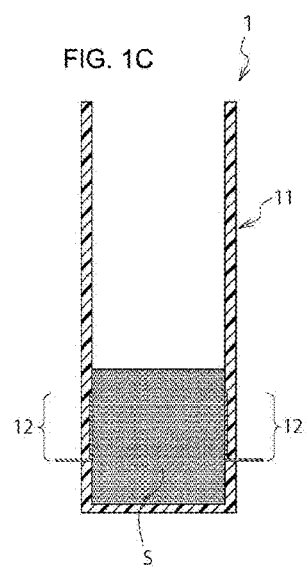
FIG. 1C is an arrow end view seen from the M side of FIG. 1A.

Also, in the present technology, the biological sample holding sections 11 are designed, as illustrated in the first embodiment of FIGS. 1A to 1C, such that each of the biological sample holding sections 11 independently forms a region that can hold the biological sample S. Accordingly, the biological samples S are not mixed with each other among the plurality of biological sample holding sections 11. Therefore, the use of the electrical measuring cartridge 1 according to the embodiment of the present technology enables a plurality of electrical measurements to be performed concurrently and at high accuracy.

Furthermore, although the electrical measuring cartridge 1 according to the embodiment of the present technology illustrated in the first embodiment of FIGS. 1A to 1C has a form for performing two electrical measurements, the number of biological sample holding sections 11 can be appropriately increased or decreased, depending on the number of electrical measurements, the measurement items, the number of measurement objects (the number of specimens), and the like.

Figure 7A:
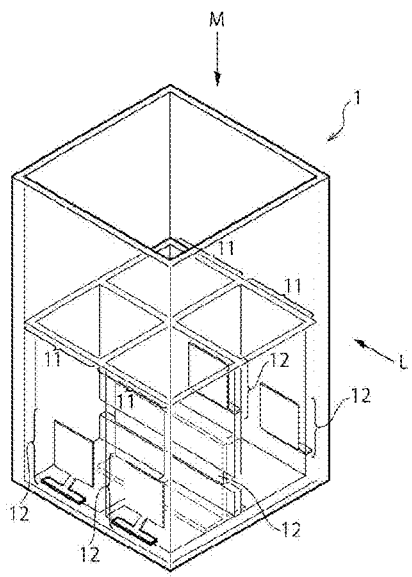
FIG. 7A is a schematic diagram schematically illustrating a sixth embodiment according to the present technology of the electrical measuring cartridge 1.
Figure 7B:
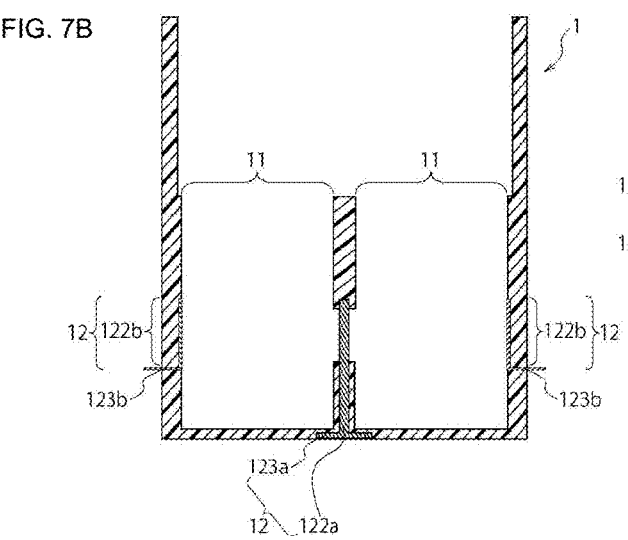
FIG. 7B is an arrow end view seen from the L side of FIG. 7A.
Figure 7C:
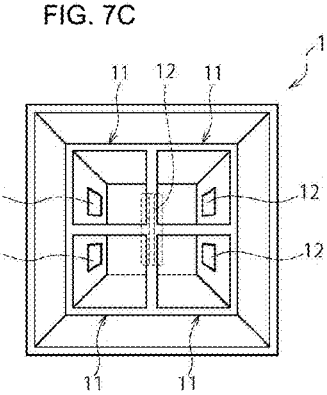
FIG. 7C is an arrow end view seen from the M side of FIG. 7A.

Specifically, the number of biological sample holding sections 11 may be set to be three which are arranged in line to provide a structure as illustrated in a second embodiment of FIG. 2, or the number of the biological sample holding sections 11 may be set to be four which are arranged in two lines to provide a structure as illustrated in a sixth embodiment of FIGS. 7A to 7C.

Also, the plurality of biological sample holding sections 11 according to the embodiment of the present technology may be structured so as to have sizes and forms identical to each other as illustrated in the first embodiment of FIGS. 1A to 1C. Alternatively, although not illustrated in the drawings, the plurality of biological sample holding sections 11 may be structured such that each thereof has a combination of a different size and a different form.

According to an embodiment of the present technology, in a state in which the biological sample S is held in the biological sample holding section 11, various kinds of electrical measurement is performed. For this reason, the biological sample holding section 11 may be configured to be sealable in a state in which the biological sample S is held. However, a time to perform various kinds of electrical measurement of the biological sample S may be delayed, and the section may not be configured to be sealable as long as the measurement is not influenced.

An introducing or encapsulating method of the biological sample S into the biological sample holding section 11 is not particularly limited, and the biological sample S can be introduced or encapsulated in an optional method depending on the form of the biological sample holding section 11. An example thereof may include, although not illustrated in the drawings, a method of introducing the biological sample S into the biological sample holding section 11 using a pipette. When a later-described closing unit 13 is disposed, other examples thereof may include: a method of introducing the biological sample S using a pipette or the like and thereafter closing with the closing unit 13 for encapsulating; and a method of sticking and inserting an injection needle from an outer surface of the biological sample holding section 11 to inject the biological sample S and thereafter covering the portion penetrated by the injection needle with grease or the like for encapsulating.

Although a material that can be used for the biological sample holding section 11 according to the embodiment of the present technology is not particularly limited, the biological sample holding section 11 can be formed with resin in the embodiment of the present technology.

In the electrical measuring cartridge 1 according to the embodiment of the present technology, the kind of resin usable in the biological sample holding section 11 is not particularly limited, and one or two or more kinds of resins that can be appropriately applied to the biological sample S may be freely selected and used. For example, a hydrophobic and insulating polymer such as polypropylene, polymethyl methacrylate, polystyrene, acryl, polysulfone, polytetrafluoroethylene, or the like, a copolymer, a blend polymer or the like may be used. In the present technology, in the above-mentioned polymers, in particular, the biological sample holding section 11 may be made of one or more kinds of resins selected from polypropylene, polystyrene, acryl, and polysulfone. Since these resins have a property such as a low coagulation activity with respect to the blood, for example, the container can be appropriately used for measurement of the biological sample containing the blood.

Also, the reagent R can be enclosed in a part of the biological sample holding section 11 according to the embodiment of the present technology. For example, as illustrated in the second embodiment of FIGS. 2A and 2B, a method may be included in which the closing unit 13 is provided for each of the plurality of biological sample holding sections 11 according to the embodiment of the present technology, so that a part of the biological sample holding section 11 is sealable so as to enclose the reagent R in the sealed portion (see W of FIGS. 2A and 2B) of the biological sample holding section 11.

The electrical measuring cartridge 1 according to the embodiment of the present technology particularly includes the plurality of biological sample holding sections 11, and is therefore excellent in the management of combinations between a plurality of measurement objects and a plurality of types of reagents R, when the plurality of types of reagents R is previously enclosed in each of the biological sample holding sections 11.

When the electrical measuring cartridge 1 according to the embodiment of the present technology is designed such that each of the plurality of biological sample holding sections 11 includes the closing unit 13, the form of the closing unit 13 is not particularly limited as long as a part of the biological sample holding section 11 is sealable, and can be freely designed depending on the type of the biological sample S or the reagent R, the measurement method, the electrical measuring apparatus to be used, and the like. Examples of the form may include a cylindrical body, a polygonal barrel having a polygonal cross section (triangle, square, or more), a circular cone, a polygonal cone having a polygonal cross section (triangle, square, or more), and one or a combination of two or more thereof.

Also, a material that can be used for the closing unit 13 is not particularly limited, and resin can be used for the formation thereof, in a similar manner to the biological sample holding section 11. It is noted that the type of resin is similar to those previously described, and therefore description thereof is omitted here.

Figure 2A:
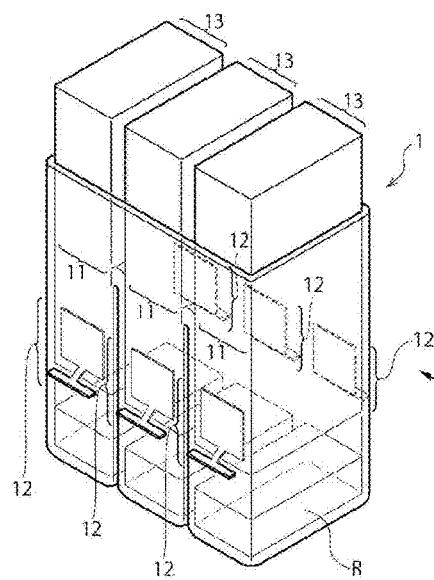
FIG. 2A is a schematic diagram schematically illustrating a second embodiment according to the present technology of the electrical measuring cartridge 1.
Figure 2B:
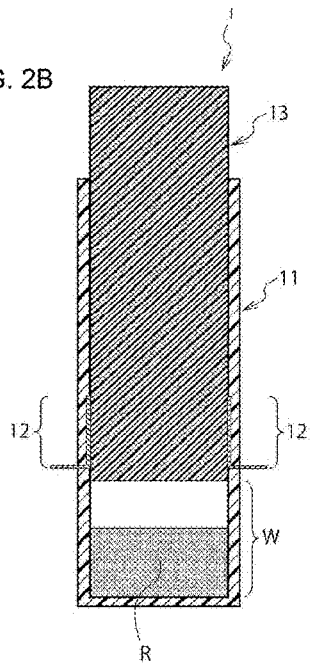
FIG. 2B is an arrow end view seen from the L side of FIG. 2A.

When the electrical measuring cartridge 1 according to the embodiment of the present technology includes the closing unit 13, the closing unit 13 is preferably designed, as illustrated in the second embodiment of FIGS. 2A and 2B, such that the closing unit 13 separates the sealed portion of the biological sample holding section 11 and the electrical conductive section 12. This is because dust or the like, in the air, which causes reduction of measurement accuracy, can be prevented from attaching to the electrical conductive section 12 or from mixing in the biological sample holding section 11. Also, when the biological sample holding section 11 is stored, transported or the like in a state of containing the reagent R, the reagent R can be inhibited from scattering onto an inner wall of the biological sample holding section 11 and onto the electrical conductive section 12. Therefore, when measuring electrical properties, the reagent amount effective for the biological sample S can be maintained, and measurement error or the like due to the reagent R remained in the electrical conductive section 12 can be reduced.

It is noted that when the electrical measuring cartridge 1 according to the embodiment of the present technology includes the closing unit 13, although not illustrated in the drawings, the electrical measuring cartridge 1 becomes, during the measurement of electrical properties, in a state where the biological sample S is held in the biological sample holding section 11, and the closing unit 13 is removed.

In the present technology, the reagent R that can be enclosed in the biological sample holding section 11 is not particularly limited, and can be freely selected. Examples thereof may include reagents in a state of gas, solid, liquid, or the like. More specifically, when the measurement object is the biological sample S containing a blood component, there may be included an anticoagulant agent, a coagulation initiator, and the like.

When the electrical measuring cartridge 1 according to the embodiment of the present technology includes the closing unit 13, the electrical measuring cartridge 1 can also be transported, stored, or the like in a state where the reagent R is previously enclosed in the biological sample holding section 11 of the electrical measuring cartridge 1 according to the embodiment of the present technology. When the reagent R is previously enclosed, merely by performing a process of removing the closing unit 13 thereby to open the electrical measuring cartridge 1 just before measuring electrical properties, and introducing the biological sample S to be measured into the biological sample holding section 11, measurement of electrical properties can be immediately initiated. For this reason, dust or the like, in the air, which causes reduction of measurement accuracy, can be prevented from mixing in the biological sample holding section 11, thus achieving the improvement of measurement accuracy. Also, working processes to the initiation of measurement decrease, thereby preventing the complication of measurement processes, and also improving the user's convenience.

The electrical measuring cartridge 1 according to the embodiment of the present technology can also store the reagent R by a method of cooling, freezing, lyophilization or the like in a state where it is enclosed, depending on the type of a reagent to be used as the reagent R.

(2) Electrical Conductive Section 12

In the electrical measuring cartridge 1 according to the embodiment of the present technology, the electrical conductive section 12 is a site that comes into contact with the biological sample S during electrical measurement and is used for applying a necessary voltage to the biological sample S. Also, the electrical measuring cartridge 1 according to the embodiment of the present technology includes a pair of electrical conductive sections 12 previously fixed to each of the plurality of biological sample holding sections 11. For this reason, a plurality of electrical measurements can be concurrently performed, and a measurement mechanism of the electrical measuring apparatus can also be inhibited from being complicated.

Also, since the pair of electrical conductive sections 12 is provided for each of the plurality of biological sample holding sections 11, when measuring electrical properties using the electrical measuring cartridge 1 according to the embodiment of the present technology, electrical measurements can also be performed while appropriately varying measurement conditions such as a voltage for each electrical conductive section 12 fixed to each biological sample holding section 11, depending on the type of the biological sample S and the measurement item. Thus, the user's convenience when measuring electrical properties improves.

In the present technology, although a method of fixing the electrical conductive section 12 to the biological sample holding section 11 is not particularly limited, a method of integrally molding the biological sample holding section 11 and the electrical conductive section 12 in a state where a part of the electrical conductive section 12 is embedded in the biological sample holding section 11 is preferred.

For example, when the electrical conductive section 12 is fixed to the biological sample holding section 11 with an adhesive, some type of adhesive used may cause the properties of the biological sample S to be adversely affected. As a more specific example, when measuring the electrical properties of blood as the biological sample S, some type of adhesive used may promote blood coagulation activity, thus adversely affecting the intended measurement. However, the adverse effect by a fixing material such as an adhesive on the biological sample S can be eliminated by employing a method of integrally molding the biological sample holding section 11 and the electrical conductive section 12, that is, a method of fixing the biological sample holding section 11 and the electrical conductive section 12 without using a fixing material such as an adhesive. As a result, the measurement accuracy when measuring electrical properties improves.

Even if a fixing material having less effect on the biological sample S is used, an adhesion process with the fixing material is added when manufacturing the cartridge for containing a biological sample, thus raising a problem that productivity is poor. However, when the method of integrally molding the biological sample holding section 11 and the electrical conductive section 12 is employed, the adhesion process does not have to be separately provided, in addition to the molding process of the biological sample holding section 11. As a result, manufacture of the electrical measuring cartridge 1 becomes easier, and the electrical measuring cartridge 1 according to the embodiment of the present technology can be produced at low cost and in large amounts.

Also, there is a method of measuring electrical properties in a state where an electrode is inserted from an outside into a cartridge that contains a biological sample. However, in this method, there is a problem that a difference in insertion amount of an electrode into a biological sample causes measurement error. However, the electrical measuring cartridge 1 according to the embodiment of the present technology includes the electrical conductive section 12 previously fixed to each of the plurality of biological sample holding sections 11. Thus, the measurement error due to a difference in insertion amount of an electrode into a biological sample can be eliminated. Therefore, the measurement accuracy during electrical measurement improves.

Furthermore, since the electrical conductive section 12 is previously fixed to each of the plurality of biological sample holding sections 11, a relative positioning mechanism between an electrode and a cartridge that contains a biological sample, or the like does not have to be disposed to an apparatus side, thus achieving the simplification of a structure on the apparatus side. This can also contribute to the realization of a miniaturized electrical measuring apparatus and a reduced cost of the apparatus, a simplified manufacturing process of the electrical measuring cartridge 1, and the like.

In the present technology, a specific method of integrally molding the biological sample holding section 11 and the electrical conductive section 12 is not particularly limited, and an optional method can be used. For example, when the biological sample holding section 11 is formed of resin, the electrical conductive section 12 is disposed at a prescribed position when the resin is solidified from a molten state, thereby enabling the biological sample holding section 11 and the electrical conductive section 12 to be integrally molded. A more specific example thereof may include a method of integrally molding the biological sample holding section 11 and the electrical conductive section 12 by a so-called insert molding in which the electrical conductive section 12 is inserted in a mold and resin is injected around the electrical conductive section 12 to unify the electrical conductive section 12 with the resin.

Since the electrical conductive section 12 is fixed concurrently when the biological sample holding section 11 is molded as described above, a manufacturing process of the electrical measuring cartridge 1 can be simplified. Therefore, the electrical measuring cartridge 1 according to the embodiment of the present technology can be produced at low cost and in large amounts.

The electrical conductive section 12 is made of a material having electrical conductivity. In the electrical measuring cartridge 1 according to the embodiment of the present technology, the kind of material having electrical conductivity used in the electrical conductive section 12 is not particularly limited, and one or two or more kinds of materials that can be appropriately applied to electrical measurement of the biological sample S can be freely selected and used. For example, titanium, aluminum, stainless steel, platinum, gold, copper, graphite, or the like may be used. In the present technology, among the materials, in particular, the electrical conductive section 12 may be made of a material having electrical conductivity and including titanium. Since titanium has a property such as a low coagulation activity with respect to the blood, for example, titanium can be appropriately used for measurement of the biological sample S containing the blood.

Also, in the electrical measuring cartridge 1 according to the embodiment of the present technology, the number of electrical conductive sections 12 fixed to each of the biological sample holding sections 11 can be freely designed for one biological sample holding section 11 depending on the intended electrical measurement method or the like. For example, when measuring permittivity and impedance of the biological sample S, a pair or more of electrical conductive sections 12 can be designed for one biological sample holding section 11.

Furthermore, the arrangement, form or the like of the electrical conductive section 12 is also not particularly limited, and can be freely designed depending on the form of the biological sample holding section 11, the measurement method, the electrical measuring apparatus to be used, and the like, as long as it can apply a necessary voltage to the biological sample S. In the present technology, especially, in order to improve measurement efficiency, as illustrated in the first embodiment of FIGS. 1A to 1C, a connection location between the biological sample holding section 11 and the electrical conductive section 12 preferably comes in planar contact with the biological sample S. For example, as illustrated in a fourth embodiment of FIGS. 4A and 4B, when a step exists on an inner wall of the biological sample holding section 11, air bubbles remain in the stepped portion (see a broken line portion X of FIG. 4B), and the concentration of a reagent varies in the stepped portion, thus possibly having adverse effects on the measurement value. Therefore, by integrally molding the biological sample holding section 11 and the electrical conductive section 12 so that the connection location becomes smooth as in the first embodiment of FIGS. 1A to 1C, the adverse effects due to air bubbles and the varied concentration of a sample can be eliminated, and the measurement accuracy during electrical measurement can be improved.

In addition, when the electrical measuring cartridge 1 according to the embodiment of the present technology includes the one or more pairs of the electrical conductive section 12, the electrical conductive section 12 may be disposed in parallel while measuring the electrical properties of the biological sample S. However, for example, in consideration of release characteristics or the like when the insert molding or the like is performed, the respective electrical conductive section 12 can be disposed in a state in which several inclinations are provided.

Also, although very rare, a difference in distortion between a resin and an electrical conduction material may cause the biological sample S to leak from a boundary between the biological sample holding section 11 and the electrical conductive section 12, depending on storage conditions such as temperatures and the measurement conditions. Therefore, the electrical conductive section 12 includes, as illustrated in a fifth embodiment of FIGS. 5A and 5B, a meandering portion (see a broken line portion Y of FIG. 5B) in a part of the structure where the electrical conductive section 12 is fixed to the biological sample holding section 11, so as to inhibit the leaking of the biological sample S from the boundary between the biological sample holding section 11 and the electrical conductive section 12 more surely than the first embodiment (see FIG. 1C) of FIGS. 1A to 1C which does not include a meandering portion.

Also, since the electrical conductive section 12 includes a meandering portion as described above, the biological sample holding section 11 and the electrical conductive section 12 are more firmly fixed to each other, thus enabling the robust electrical measuring cartridge 1 to be formed.

Figure 5A:
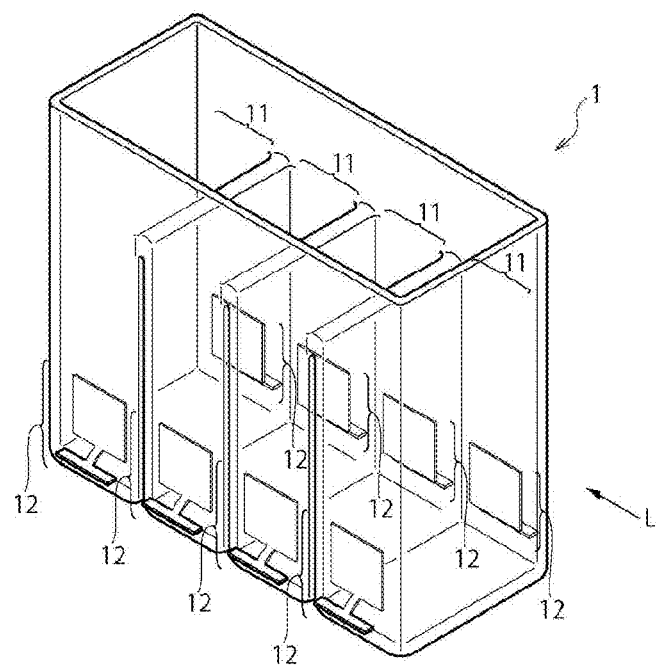
FIG. 5A is a schematic diagram schematically illustrating a fifth embodiment according to the present technology of the electrical measuring cartridge 1.
Figure 5B:
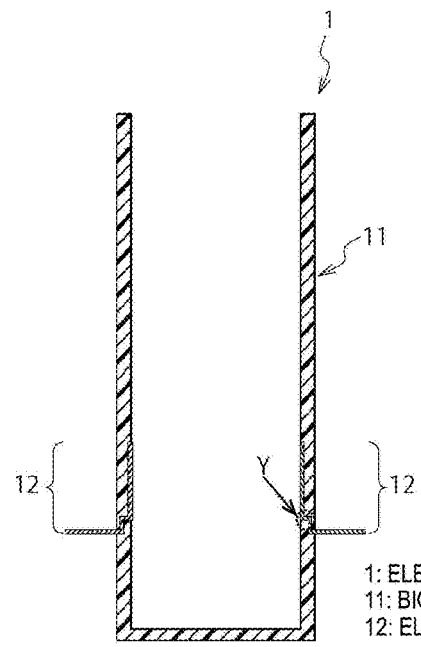
FIG. 5B is an arrow end view seen from the L side of FIG. 5A.

Furthermore, the electrical conductive sections 12 according to the embodiment of the present technology are, as illustrated in the fifth embodiment of FIGS. 5A and 5B, fixed to at least two or more biological sample holding sections 11, and the electrical conductive sections 12 can be aligned along an identical plane of the electrical measuring cartridge 1.

Figure 3:
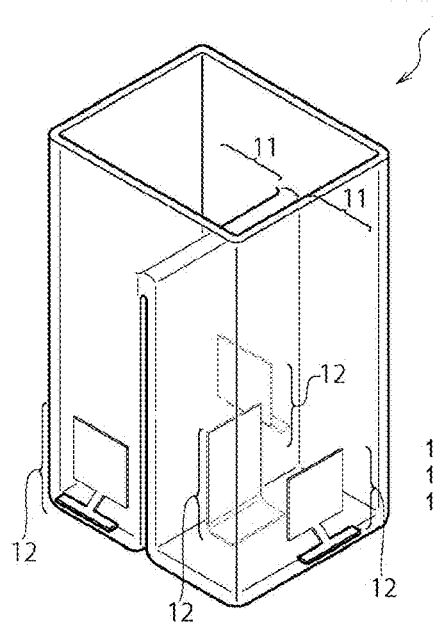
FIG. 3 is a schematic diagram schematically illustrating a third embodiment according to the present technology of the electrical measuring cartridge 1.

Here, FIG. 3 is a schematic diagram schematically illustrating a third embodiment of the electrical measuring cartridge 1 according to the embodiment of the present technology, and is an example in which the electrical conductive sections 12 are not arranged along an identical plane of the electrical measuring cartridge 1. Also, FIG. 4A is a schematic diagram schematically illustrating a fourth embodiment of the electrical measuring cartridge 1 according to the embodiment of the present technology, and is an example in which the electrical conductive sections 12 are arranged, but not aligned, along an identical plane of the electrical measuring cartridge 1.

Figure 4A:
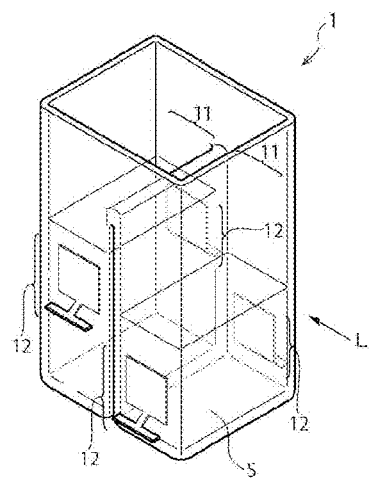
FIG. 4A is a schematic diagram schematically illustrating a fourth embodiment according to the present technology of the electrical measuring cartridge 1.
Figure 4B:
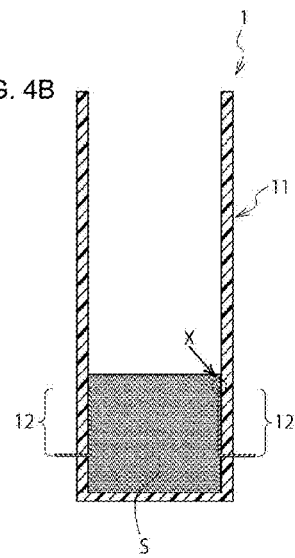
FIG. 4B is an arrow end view seen from the L side of FIG. 4A.

When the electrical measuring cartridge 1 according to the embodiment of the present technology is the fifth embodiment of FIGS. 5A and 5B, the complication of a measurement mechanism of an electrical device can be inhibited, and the measurement accuracy during electrical measurement can be improved, compared to the third embodiment of FIG. 3 and the fourth embodiment of FIGS. 4A and 4B. Also, this can contribute to the realization of a miniaturized electrical measuring apparatus and a reduced cost of the apparatus, a simplified manufacturing process of the electrical measuring cartridge 1, and the like.

(a) Linkage Section 121

Figure 6:
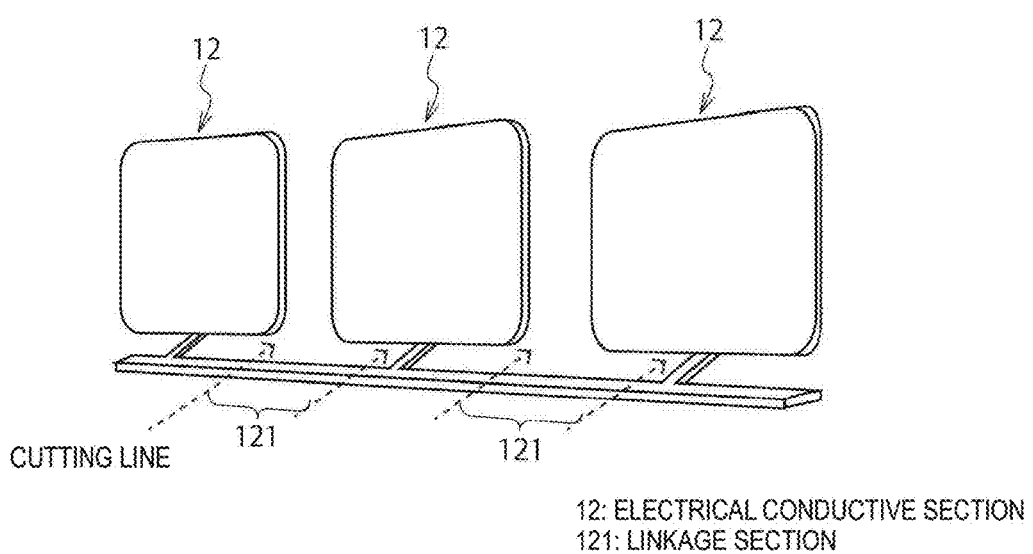
FIG. 6 is a schematic diagram schematically illustrating a state (an electrode array) in which the electrical conductive sections 12 according to an embodiment of the present technology are partly linked to each other via linkage sections 121.

FIG. 6 is a schematic diagram schematically illustrating a state (an electrode array) where the plurality of electrical conductive sections 12 are partly linked to each other via linkage sections 121. The plurality of electrical conductive sections 12 according to the embodiment of the present technology can be molded by being molded in a state where parts of the electrical conductive sections 12 are linked to each other, and then cutting off the linkage sections 121 along cutting lines (see broken line arrows of FIG. 6).

A specific example thereof may include a method of molding the plurality of electrical conductive sections 12 by a method of press processing or the like, into a state of being partly linked to each other via the linkage sections 121 which have been previously formed so as to be easily cut and to a degree such that rapture is not caused, and then cutting off the linkage sections 121 by simple processing. The reason why the linkage sections 121 are previously formed so as to be easily cut is that the electrical conductive sections 12 can be easily separated from each other by simple processing. Also, the reason why the linkage sections 121 are formed to a degree such that rapture is not caused is that when cutting off the linkage sections 121 after integrally molding the biological sample holding sections 11 and the electrical conductive sections 12 by insert molding, the resin flow, mold sliding, and the like do not cause the linkage sections 121 to easily rapture.

Also, in the present technology, although the simple processing for cutting off the linkage sections 121 is not particularly limited, examples thereof may include a method using laser and a method by press processing.

Although a timing when the linkage sections 121 are cut off in the manufacturing process of the electrical measuring cartridge 1 according to the embodiment of the present technology is not particularly limited, it is preferred that the cutting-off is performed after the electrical conductive sections 12 have been integrally molded to the biological sample holding sections 11. An example thereof when the biological sample holding sections 11 and the electrical conductive sections 12 are integrally molded by insert molding may include a method of holding an electrode array in a mold or the like and insert molding the electrical conductive sections 12 to the biological sample holding sections 11, and then cutting off the linkage sections 121.

Since the linkage sections 121 are cut off at the above-described timing, the electrical conductive sections 12 do not have to be subjected to the process of being fixed one by one to the plurality of biological sample holding sections 11 according to the embodiment of the present technology in the manufacturing process of the electrical measuring cartridge 1. Thus, the electrical conductive sections 12 can be efficiently fixed to each of the plurality of biological sample holding sections 11. Therefore, the simplified manufacturing process of the electrical measuring cartridge 1 can be realized.

Also, for example, when the biological sample holding sections 11 and the electrical conductive sections 12 are integrally molded by insert molding, the decrease of the number of parts during insert-molding reduces the number of processing objects in the manufacturing process, and facilitates the manufacture of the electrical measuring cartridge 1. Therefore, the electrical measuring cartridge 1 according to the embodiment of the present technology can be produced at low cost and in large amounts.

Furthermore, when the plurality of electrical conductive sections 12 are aligned along an identical plane of the electrical measuring cartridge 1 as illustrated in the fifth embodiment of FIGS. 5A and 5B, cutting-off of the linkage sections 121 at the above-described timing allows the plurality of electrical conductive sections 12 to be easily aligned at predetermined positions of the biological sample holding sections 11. Therefore, the manufacturing process of the electrical measuring cartridge 1 can be simplified, thus improving productivity.

In addition, determination on cutting locations of the electrode array according to the purposes of electrical measurements, the estimated magnitude of signals, and the like, enables the electrical measuring cartridge 1 according to the embodiment of the present technology to be changed to have an optional conductive pair.

Specifically, of the plurality of electrical conductive sections 12 according to the embodiment of the present technology, an optional part of the electrical conductive sections 12 may be remained in a state of being linked to each other via the linkage sections 121, thus allowing the optional part of the electrical conductive sections 12 to be measured at the same potential. This is because when measuring electrical properties, there are some cases where measurement at the same potential has better measurement efficiency from the viewpoint of a signal/noise ratio, for example, in measurement with small signals.

Also, cutting-off of the linkage sections 121 at the above-described timing to determine an optional conductive pair is useful when, for example, desiring to use the electrical measuring cartridge 1 according to the embodiment of the present technology in the measurement with small signals.

For example, prior to the cutting-off of the linkage sections 121, the electrical measuring cartridge 1 can be manufactured in the same manufacturing process as when desired to be used in another measurement. Therefore, while the manufacturing process of the electrical measuring cartridge 1 is simplified, the structure of the electrical measuring cartridge 1 can be optimized according to the intended electrical measurement or the like.

The electrical conductive section 12 according to the embodiment of the present technology may include an electrode section 122 and a connection section 123. Hereinafter, each section will be described in detail.

(b) Electrode Section 122

The electrode section 122 is a site that comes into contact with the biological sample S during electrical measurement to apply a necessary voltage to the biological sample S. In the electrical measuring cartridge 1 according to the embodiment of the present technology, the number of electrode sections 122 fixed to each of the biological sample holding sections 11 can be freely designed for one biological sample holding section 11 depending on the intended electrical measurement method or the like. For example, when measuring permittivity and impedance of the biological sample S, a pair or more of electrode sections 122 can be designed for one biological sample holding section 11.

Also, the arrangement, form or the like of the electrode section 122 is not particularly limited, and can be freely designed depending on the form of the biological sample holding section 11, the measurement method, the electrical measuring apparatus to be used, and the like, as long as it can apply a necessary voltage to the biological sample S. In the present technology, especially, in order to improve measurement efficiency, the electrode section 122 preferably comes in planar contact with the biological sample S. For example, a portion, of the electrode section 122, that comes into contact with the biological sample S, may be formed with a wide width, thus enabling planar contact with the biological sample S.

The electrode sections 122 according to the embodiment of the present technology can be partly used, as illustrated in a sixth embodiment of FIGS. 7A to 7C, as a common electrode (see 122a of FIGS. 7A to 7C). When the electrode sections 122 are partly used as a common electrode 122a, the number of electrode sections 122 for which the processing to the plurality of biological sample holding sections 11 is necessary can be reduced. Therefore, the number of processing objects in the manufacturing process of the electrical measuring cartridge 1 decreases, thus enabling the simplification of the manufacturing process. Therefore, the electrical measuring cartridge 1 according to the embodiment of the present technology can be produced at low cost and in large amounts.

Also, when the electrode sections 122 are partly used as the common electrode 122a, heat transfer conditions to the electrode sections 122 can be partly set as being equivalent. Accordingly, the improvement in measurement accuracy during electrical measurement is realized.

On the other hand, an electrode that is paired with the common electrode 122a has to be independent. Therefore, the electrode that is paired with the common electrode 122a has to be processed to be separated. It is noted that the electrode to be paired with the common electrode 122a may be the electrode section 122b as in the sixth embodiment of FIGS. 7A to 7C or a later-described third embodiment of FIG. 10, or may be the electrical conductive section 12 the whole of which functions as the electrode section 122 as in a fifth embodiment of FIG. 12.

(c) Connection Section 123

The connection section 123 is a site that is electrically connected to an external circuit. The arrangement, form or the like of the connection section 123 is not particularly limited, and can be designed to have an optional form depending on the intended electrical measuring method and the like, as long as it can be electrically connected to an external circuit. Hereinafter, an arrangement example of the electrode section 122 and the connection section 123 will be described in detail.

First Embodiment

Figure 8:
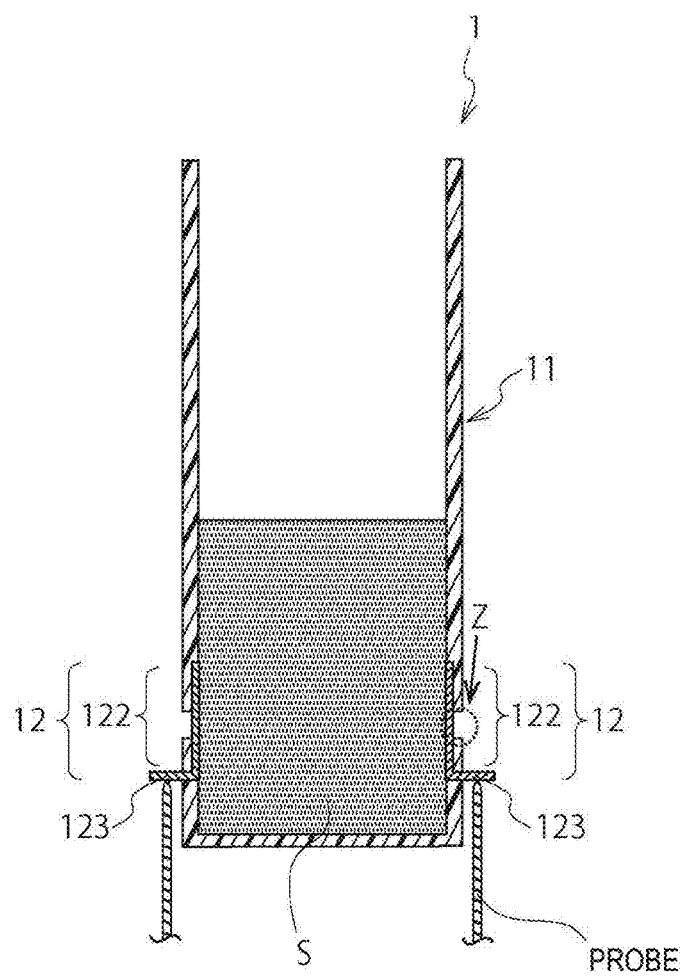
FIG. 8 is an end schematic diagram schematically illustrating a first embodiment according to the present technology of an electrode section 122 and a connection section 123.

FIG. 8 is an end schematic diagram schematically illustrating a first embodiment of the electrode section 122 and the connection section 123 according to the embodiment of the present technology, and is an example in which the pair of electrical conductive sections 12 are arranged so as to run along an inner wall of the biological sample holding section 11. More specifically, in the example, in a state where a portion of the electrical conductive section 12 is embedded in a side wall of the biological sample holding section 11, the electrode section 122 is disposed inside the biological sample holding section 11, and the connection section 123 is disposed outside the biological sample holding section 11.

In the first embodiment of FIG. 8, the connection section 123 is disposed in a state of projecting from the side wall of the biological sample holding section 11. When measuring electrical properties in the first embodiment, electrical connection is performed by bringing a probe of an apparatus side into contact with a part of each connection section 123 from a side of the biological sample holding section 11 as illustrated in FIG. 8.

Also, the electrical measuring cartridge 1 according to the embodiment of the present technology may have a structure in which resin or the like is not provided on an outside portion of each of the pair of electrical conductive sections 12, as illustrated in the first embodiment of FIG. 8. With such a structure, for example, the electrical conductive section 12 can be positioned and fixed using a magnetic unit such as a magnet when molding the biological sample holding section 11, thus enabling the electrical conductive section 12 to be positioned at a predetermined position on the electrical measuring cartridge 1. It is noted that a fixing mechanism of the electrical conductive section 12 from an outside of a cartridge is not limited to the above-described magnetic unit, and any unit can be used as long as it can fix the electrical conductive section 12 from an outside of a cartridge.

Furthermore, at least a part of the electrical conductive section 12 may be allowed to function as a holding section for arranging the electrical conductive section 12 at a predetermined position of the biological sample holding section 11 during integral molding, thereby enabling easy manufacture of the electrical measuring cartridge 1 in which the electrical conductive section 12 is precisely positioned at a predetermined position. Also, fixing the electrical conductive section 12 from an outside of a cartridge while molding the biological sample holding section 11 can also inhibit deformation of the electrical conductive section 12.

Furthermore, when the electrical measuring cartridge 1 according to the embodiment of the present technology has a structure in which resin or the like is not provided on the cartridge outside portion of each of the pair of electrical conductive sections 12 as illustrated in the first embodiment of FIG. 8, electrical connection can also be performed by bringing a probe of an apparatus side into contact with a part of each electrical conductive section 12, through a portion (see a broken line portion Z of FIG. 8), on the cartridge outside portion of each of the pair of electrical conductive sections 12, where resin or the like is not provided, while measuring electrical properties.

It is noted that when the electrical measuring cartridge 1 according to the embodiment of the present technology has a structure in which resin or the like is not provided on the cartridge outside portion of the electrical conductive section 12, although not illustrated in the drawings, the electrical conductive section 12 constituting the electrical measuring cartridge 1 may be the electrical conductive section 12 the whole of which functions as the electrode section 122. Even in this case, electrical connection is performed by bringing a probe of an apparatus side into contact with a part of the electrical conductive section 12, through a portion, of the cartridge outside portion of each of the pair of electrical conductive sections 12, where resin or the like is not provided.

Second Embodiment

Figure 9:
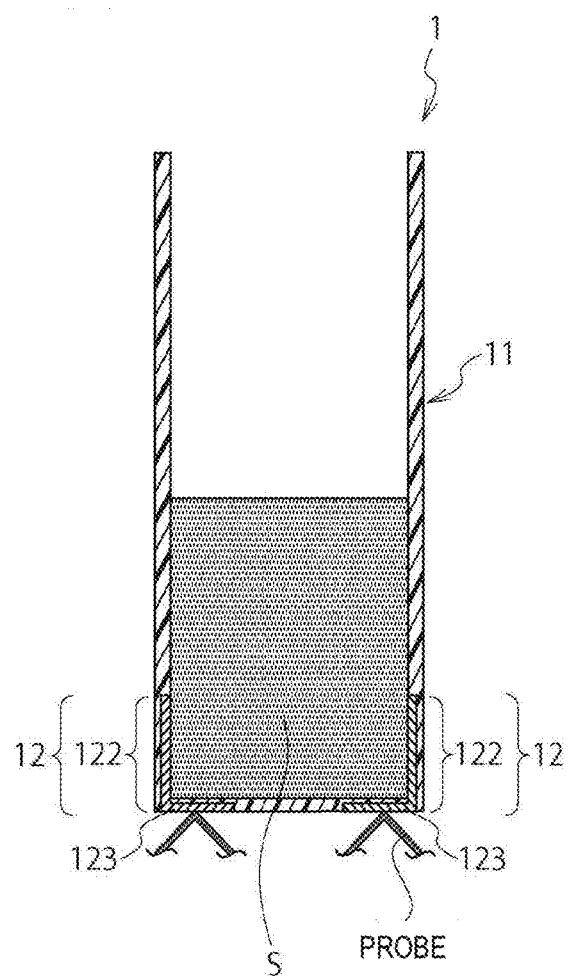
FIG. 9 is an end schematic diagram schematically illustrating a second embodiment according to the present technology of an electrode section 122 and a connection section 123.

FIG. 9 is an end schematic diagram schematically illustrating a second embodiment of the electrode section 122 and the connection section 123 according to the embodiment of the present technology, and is an example in which each of the pair of electrical conductive sections 12 is arranged so as to run along a vicinity of a lower inner wall of the biological sample holding section 11. More specifically, in the example, in a state where the electrical conductive section 12 is embedded around a lower side wall of the biological sample holding section 11, the electrode section 122 and the connection section 123 are disposed inside the biological sample holding section 11.

In the second embodiment of FIG. 9, the connection section 123 is disposed in a state of being embedded in a bottom wall portion of the biological sample holding section 11. When measuring electrical properties in the second embodiment, electrical connection is performed by bringing a probe of an apparatus side into contact with a part of each connection section 123 from a bottom of the biological sample holding section 11 as illustrated in FIG. 9.

In the present technology, the form of electrical connection by a probe of an apparatus side may be freely selected depending on the arrangement, form and the like of the electrode section 122 and the connection section 123. For example, as described above, a probe of an apparatus side may come into contact with a part of the connection section 123 through a side wall, a bottom or the like of the electrical measuring cartridge 1, so as to bring the electrical measuring cartridge 1 into contact with an electrical apparatus.

Also, a method of bringing the probe of an apparatus side into contact with a part of the connection section 123 can be appropriately and freely selected. Examples thereof may include a method of designing a probe so as to contract by itself and applying an appropriate load thereby to maintain a state of being in contact with a part of the connection section 123, and a method of using a plate spring or the like to come into contact with a part of the connection section 123.

Third Embodiment

Figure 10:
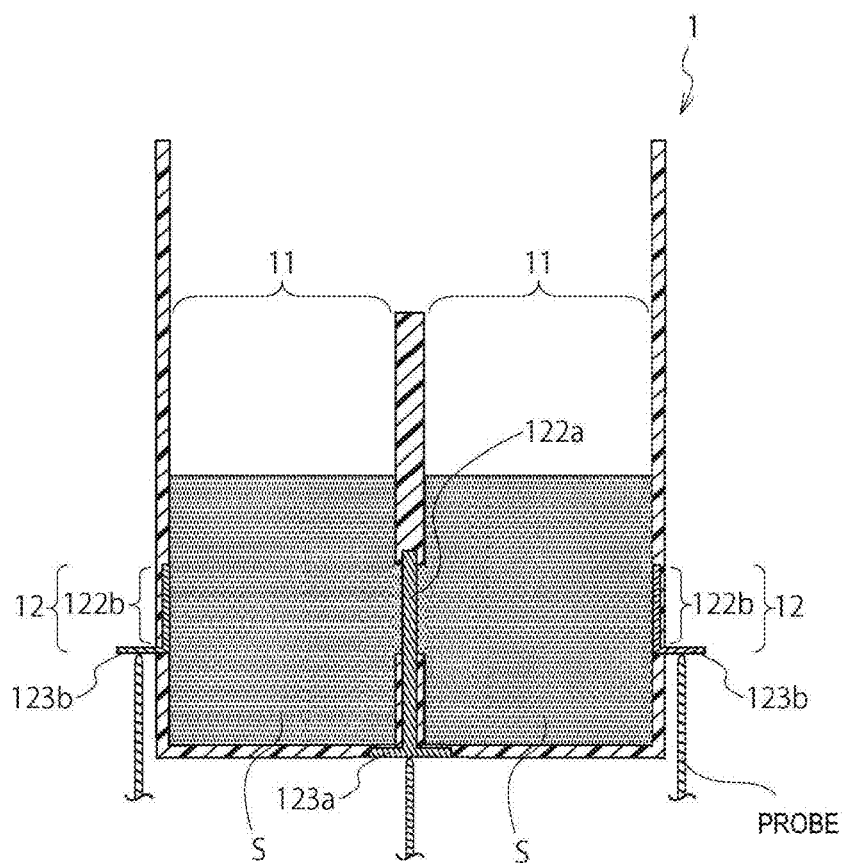
FIG. 10 is an end schematic diagram schematically illustrating a third embodiment according to the present technology of an electrode section 122 and a connection section 123.

FIG. 10 is an end schematic diagram schematically illustrating a third embodiment of the electrode section 122 and the connection section 123 according to the embodiment of the present technology. FIG. 10 is an example in which a part of the electrode sections 122 according to the embodiment of the present technology is set as the common electrode 122a. More specifically, in the example, the common electrode 122a is disposed so as to lie between side walls of the plurality of biological sample holding sections 11, and the connection section 123a linked to the common electrode 122a is disposed so as to lie between bottom walls of the plurality of biological sample holding sections 11. Furthermore, the electrode section 122b to be paired with the common electrode 122a is disposed inside the biological sample holding section 11, and the connection section 123b linked to the electrode section 122b is disposed outside the biological sample holding section 11. It is noted that in the third embodiment, an electrode to be paired with the common electrode 122a is the electrode section 122b.

In the third embodiment of FIG. 10, the connection section 123a linked to the common electrode 122a is disposed in a state of being embedded so as to lie between the bottom walls of the plurality of biological sample holding sections 11, and the connection section 123b linked to the electrode section 122b is disposed in a state of projecting from the side wall of the biological sample holding section 11. When measuring electrical properties in the third embodiment, electrical connection is performed by bringing a probe of an apparatus side into contact with a part of the connection section 123a from the bottom of the biological sample holding section 11, and a part of the connection section 123b from the side of the biological sample holding section 11, as illustrated in FIG. 10.

Fourth Embodiment

Figure 11:
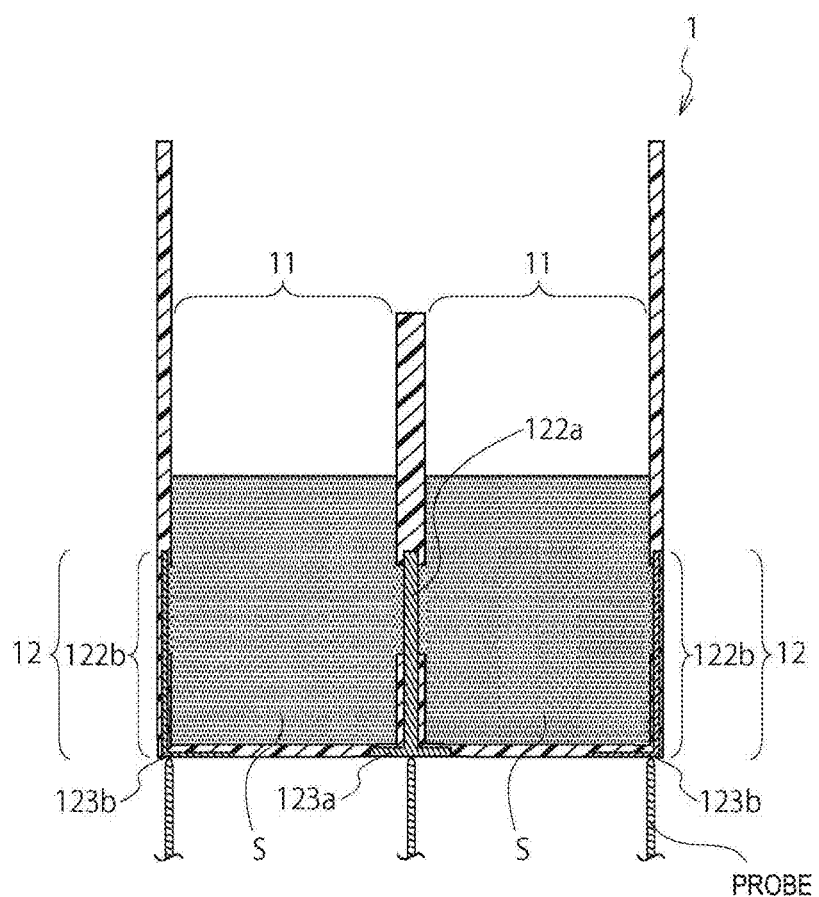
FIG. 11 is an end schematic diagram schematically illustrating a fourth embodiment according to the present technology of an electrode section 122 and a connection section 123.

FIG. 11 is an end schematic diagram schematically illustrating a fourth embodiment of the electrode section 122 and the connection section 123 according to the embodiment of the present technology. FIG. 11 is an example in which a part of the electrode sections 122 according to the embodiment of the present technology is set as the common electrode 122a. More specifically, in the example, the common electrode 122a is disposed so as to lie between side walls of the plurality of biological sample holding sections 11, and the connection section 123a linked to the common electrode 122a is disposed so as to lie between bottom walls of the plurality of biological sample holding sections 11. Furthermore, the electrode section 122b to be paired with the common electrode 122a and the connection section 123b linked to the electrode section 122b are disposed inside the biological sample holding section 11.

In the fourth embodiment of FIG. 11, the connection section 123a linked to the common electrode 122a is disposed in a state of being embedded so as to lie between the bottom walls of the plurality of biological sample holding sections 11, and the connection section 123b linked to the electrode section 122b is also disposed in a state of being embedded in the bottom wall of the biological sample holding section 11. When measuring electrical properties in the fourth embodiment, electrical connection is performed by bringing a probe of an apparatus side into contact with a part of each connection section (123a and 123b) from the bottom of the biological sample holding section 11 as illustrated in FIG. 11.

Fifth Embodiment

Figure 12:
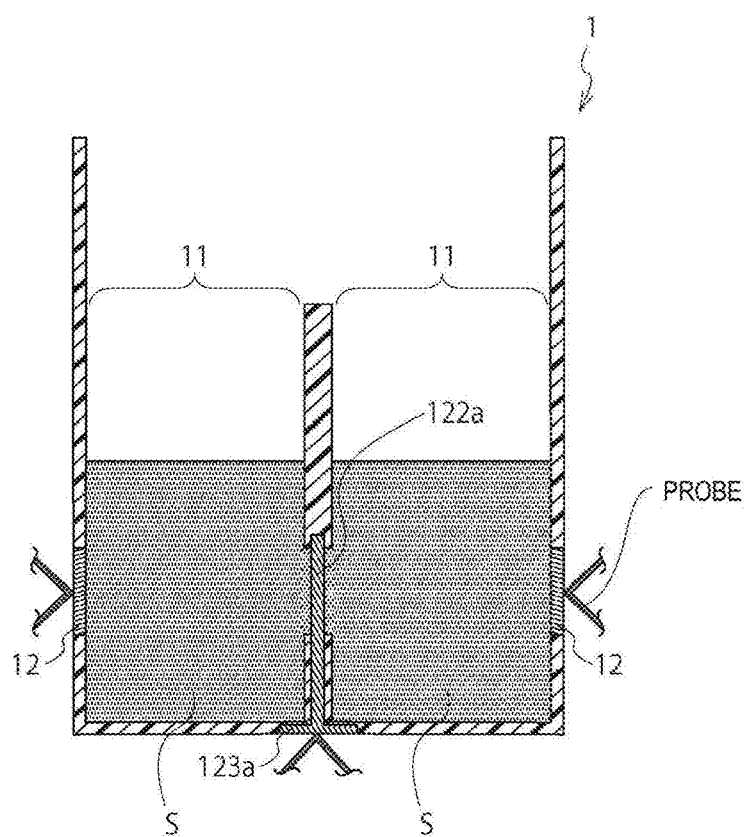
FIG. 12 is an end schematic diagram schematically illustrating a fifth embodiment according to the present technology of an electrode section 122 and a connection section 123.

FIG. 12 is an end schematic diagram schematically illustrating a fifth embodiment of the electrode section 122 and the connection section 123 according to the embodiment of the present technology. FIG. 12 is an example in which a part of the electrode sections 122 according to the embodiment of the present technology is set as the common electrode 122a. More specifically, in the example, the common electrode 122a is disposed so as to lie between side walls of the plurality of biological sample holding sections 11, and the connection section 123a linked to the common electrode 122a is disposed so as to lie between bottom walls of the plurality of biological sample holding sections 11. Furthermore, the electrical conductive section 12 to be paired with the common electrode 122a is disposed inside the biological sample holding section 11. It is noted that in the fifth embodiment, an electrode to be paired with the common electrode 122a is the electrical conductive section 12 the whole of which functions as the electrode section 122.

In the fifth embodiment of FIG. 12, the connection section 123a linked to the common electrode 122a is disposed in a state of being embedded so as to lie between the bottom walls of the plurality of biological sample holding sections 11, and the electrical conductive section 12 to be paired with the common electrode 122a is disposed in a state of forming a part of the side wall of the biological sample holding section 11. When measuring electrical properties in the fifth embodiment, electrical connection is performed by bringing a probe of an apparatus side into contact with a part of the connection section 123a from the bottom of the biological sample holding section 11, and a part of the electrical conductive section 12 from the side of the biological sample holding section 11, as illustrated in FIG. 12.

As described above, in the electrical measuring cartridge 1 according to the embodiment of the present technology, even when a part of the electrode sections 122 according to the embodiment of the present technology is configured as the common electrode 122a, the form, arrangement or the like of the electrode section 122, the connection section 123, or the electrical conductive section 12 the whole of which functions as the electrode section 122 can be freely designed depending on the intended electrical measuring method or the like. Also, the form of electrical connection by the probe of an apparatus side, and the method of bringing the probe of an apparatus side into contact with a part of the connection section 123 can be appropriately and freely selected.

(3) Biological Sample S

The biological sample S that can be used as the measurement target in the embodiment of the present technology is not particularly limited, and may be freely selected. For example, the biological sample S in a liquid phase may be provided. More specifically, the biological sample S containing blood ingredients such as whole blood, blood plasma, a diluted solution thereof, and/or drug additives, or the like, may be provided.

(4) Others

The electrical measuring cartridge 1 according to the embodiment of the present technology can be produced at low cost and in large amounts as described above. Taking advantage of such characteristics, for example, the electrical measuring cartridge 1 according to the embodiment of the present technology may be configured as being disposable. When the electrical measuring cartridge 1 according to the embodiment of the present technology is configured as being disposable, time and labor such as washing of a cartridge can be saved, thus achieving the improvement of user's convenience and the efficient measurement of electrical properties. Also, measurement error due to another biological sample S remained in the cartridge can be inhibited from occurring, thus also realizing the improvement of measurement accuracy during electrical measurement.

2. Electrical Measuring Apparatus 10

Figure 13:
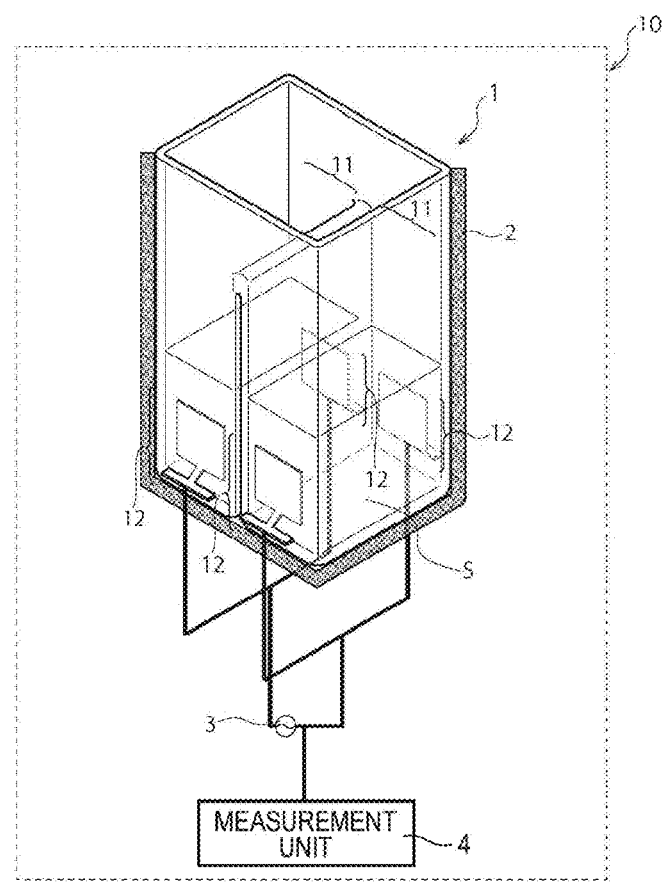
FIG. 13 is a schematic diagram schematically illustrating a first embodiment according to the present technology of an electrical measuring apparatus 10.

FIG. 13 is a schematic diagram schematically illustrating a first embodiment of an electrical measuring apparatus 10 according to the embodiment of the present technology. In this embodiment, the previously-described electrical measuring cartridge 1 according to the first embodiment is used. The electrical measuring apparatus 10 according to the embodiment of the present technology of FIG. 13 roughly includes at least the previously-described electrical measuring cartridge 1, a cartridge insertion section 2, an application unit 3, and a measurement unit 4. Hereinafter, each component will be described in detail. It is noted that the electrical measuring cartridge 1 is similar to that previously described, and therefore description thereof is omitted here.

(1) Cartridge Insertion Section 2

Into the cartridge insertion section 2 according to the embodiment of the present technology, the electrical measuring cartridge 1 according to the embodiment of the present technology is inserted. The cartridge insertion section 2 can be freely designed depending on the form of the electrical measuring cartridge 1, and the like.

Also, the cartridge insertion section 2 may include a temperature adjusting mechanism. The temperature adjusting mechanism is a mechanism that enables the temperature of the biological sample S held in the biological sample holding section 11 to be maintained constant. An example thereof may include a method of forming the cartridge insertion section 2 with a heat reserving material, so that the temperature of the biological sample S is maintained constant in a state where the electrical measuring cartridge 1 according to the embodiment of the present technology is inserted in the electrical measuring apparatus 10.

(2) Application Unit 3

The application unit 3 according to the embodiment of the present technology applies a voltage to the electrical conductive section 12 of the electrical measuring cartridge 1 according to the embodiment of the present technology. The application unit 3 applies a voltage to the electrical conductive section 12 of the electrical measuring cartridge 1 when an order to initiate measurement is received or when power of the electrical measuring apparatus 10 is input as a start point. More specifically, the application unit 3 applies an alternating current voltage having a predetermined frequency to the electrical conductive section 12 at a set measurement interval. In addition, the voltage applied by the application unit 3 may be a direct current voltage according to the measured electrical properties.

Figure 14:
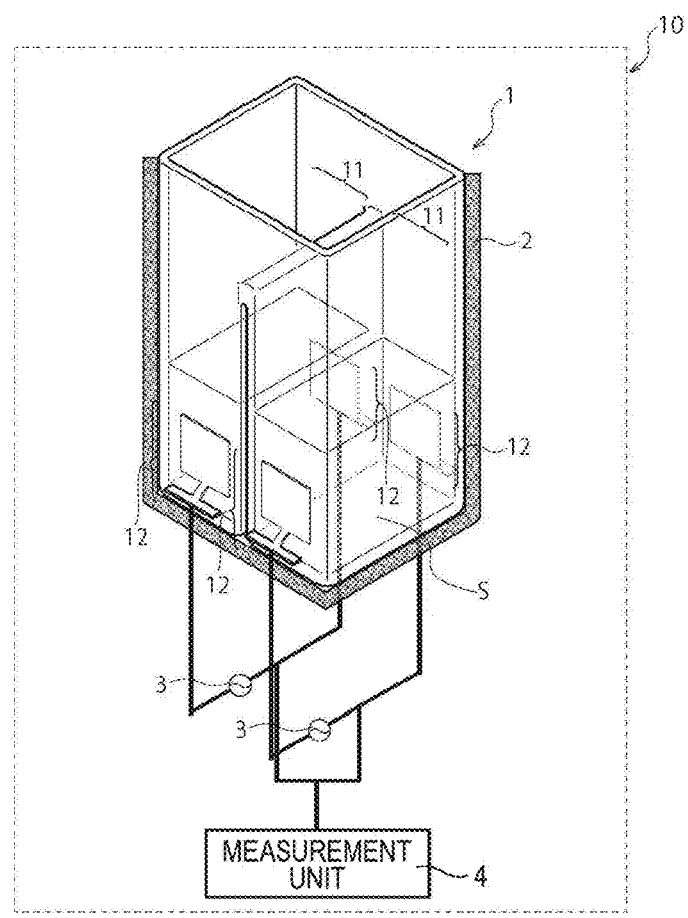
FIG. 14 is a schematic diagram schematically illustrating a second embodiment according to the present technology of an electrical measuring apparatus 10.

It is noted that the electrical measuring apparatus 10 according to the embodiment of the present technology may include one or a plurality of application units 3. Specifically, when designed as illustrated in the first embodiment of FIG. 13, the electrical conductive sections 12 fixed to the plurality of biological sample holding sections 11 of the electrical measuring cartridge 1 can be each configured to be applied with a voltage by one application unit 3. Also, when designed as illustrated in a second embodiment of FIG. 14, the electrical conductive sections 12 can be each configured to be applied with a voltage by two application units 3.

More specifically, when the electrical measuring apparatus 10 according to the embodiment of the present technology includes one application unit 3, there may be provided: a method of applying a voltage by allowing the application unit 3 to scan; a method of fixing the position of one application unit 3 and moving the electrical measuring cartridge 1 itself for applying a voltage; or a method of selecting, by switching, the electrical conductive section 12 to be actually applied with a voltage thereby to apply a voltage to each electrical conductive section 12. Also, when the electrical measuring apparatus 10 according to the embodiment of the present technology includes two or more application units 3, there may be provided, for example, a method of selecting, by switching, one or a plurality of application units 3 to be actually applied with a voltage thereby to apply a voltage.

Also, the electrical measuring apparatus 10 according to the embodiment of the present technology can be designed such that a voltage to be applied to each electrical conductive section 12 varies depending on the type of the biological sample S, the measurement method, and the like. For example, when the electrical measuring apparatus 10 according to the embodiment of the present technology include one application unit 3, there may be provided, for example, a method of allowing one application unit 3 to scan and vary a voltage when applying the voltage to each electrical conductive section 12. Also, when the electrical measuring apparatus 10 according to the embodiment of the present technology includes two or more application units 3, there may be provided, for example, a method of setting each application unit 3 at a different voltage thereby to vary the voltage.

(3) Measurement Unit 4

The measurement unit 4 according to the embodiment of the present technology measures electrical properties of the biological sample S held in the electrical measuring cartridge 1 according to the embodiment of the present technology. Specifically, electrical properties such as complex permittivity (hereinafter simply referred to as "permittivity"), frequency dispersion thereof, or the like, are measured when an order to initiate measurement is received or when power of the electrical measuring apparatus 10 is input. For example, when the permittivity is measured, the measurement unit 4 measures a current or impedance between the electrical conductive sections 12 of the electrical measuring cartridge 1 at a predetermined period, and derives permittivity from the measured value. In deriving the permittivity, a known function or relational expression showing a relation between the current or impedance and the permittivity may be used.

It is noted that the electrical measuring apparatus 10 according to the embodiment of the present technology may include one or a plurality of measurement units 4. Specifically, when designed as illustrated in the first embodiment of FIG. 13, electrical properties of each of the biological samples S held by the plurality of biological sample holding sections 11 of the electrical measuring cartridge 1 can be configured to be measured by one measurement unit 4. Also, although not illustrated in the drawings, electrical properties of each biological sample S can be configured to be measured by two or more measurement units 4.

More specifically, when the electrical measuring apparatus 10 according to the embodiment of the present technology includes one measurement unit 4, there may be provided, for example: a method of allowing one measurement unit 4 to scan thereby to measure electrical properties of each of the biological samples S held by the plurality of biological sample holding sections 11; a method of fixing the position of one measurement unit 4 and moving the electrical measuring cartridge 1 itself thereby to measure electrical properties of each biological sample S; or a method of selecting, by switching, the biological sample S to be actually subjected to measurement of electrical properties thereby to measure electrical properties of each biological sample S. Also, when the electrical measuring apparatus 10 according to the embodiment of the present technology includes two or more measurement units 4, there may be provided, for example, a method of selecting, by switching, one or a plurality of measurement units 4 that actually measure electrical properties thereby to measure the electrical properties of each biological sample S.

(4) Others

The electrical measuring apparatus 10 according to the embodiment of the present technology may further include a positioning mechanism of the electrical measuring cartridge 1 according to the embodiment of the present technology. When the position of the electrical measuring cartridge 1 is precisely set, the contact position between the electrical conductive section 12 and the application unit 3 also becomes precise, thereby achieving the improvement of user's convenience and measurement accuracy. For example, there may be provided a method of designing a positioning pin that positions the electrical measuring cartridge 1 in a height direction to the electrical measuring apparatus 10.

Further, the measuring apparatus 10 may include an analysis unit which receives electrical property data of the biological sample S derived from the measurement unit 4, and performs determination or the like of physical properties of the biological sample S. In the electrical measuring apparatus 10 according to the embodiment of the present technology, the analysis unit may be omitted, and for example, the analysis may be performed from the measured electrical property data using an external computer or the like.

Specifically, the electrical property data of the biological sample S derived from the measurement unit 4 is provided to the analysis unit at measurement intervals, and the analysis unit receives the electrical property data provided from the measurement unit 5 and starts determination or the like of the physical properties of the biological sample S. The analysis unit informs of a result of the determination or the like of the physical properties of the biological sample S and/or permittivity data. The information may be converted into, for example, a graph to be displayed on a monitor or printed on a predetermined medium.

Furthermore, the electrical measuring apparatus 10 according to the embodiment of the present technology may also include one or a plurality of analysis units, in a similar manner to the application units 3 and the measurement units 4 as previously described.

In addition, since the electrical measuring apparatus 10 includes the electrical measuring cartridge 1 according to the embodiment of the present technology, a measurement result obtained for the biological sample S held by one biological sample holding section 11 can be used for the purpose of artifact reduction when performing measurement of the biological sample S held by another biological sample holding section 11.

Specifically, for example, when measuring electrical properties of blood, which is a cell suspension, as the biological sample S, time-dependent sedimentation of cells possibly has adverse effects on a measurement result such as permittivity. Here, in general, when electrically measuring blood coagulability, the electrical measurement of blood is initiated after releasing the anticoagulation state of blood by adding the reagent R such as an aqueous solution of calcium chloride immediately before the initiation of measurement. With the use of the electrical measuring cartridge according to an embodiment of the present technology, for example, electrical measurement involving only the effect by the sedimentation of cells is performed without adding the reagent R to one biological sample holding section 11, while electrical measurement of blood cogulability also involving the effect by the sedimentation of cells is performed by adding the reagent R to another biological sample holding section 11 to release the anticoagulation state. Thereafter, one measurement result involving only the effect by the sedimentation of cells is used to correct the determination result of coagulability, thereby enabling artifact due to blood sedimentation to be reduced. Therefore, the measurement accuracy during electrical measurement can be improved.

3. Electrical Measuring Kit K

Figure 15:
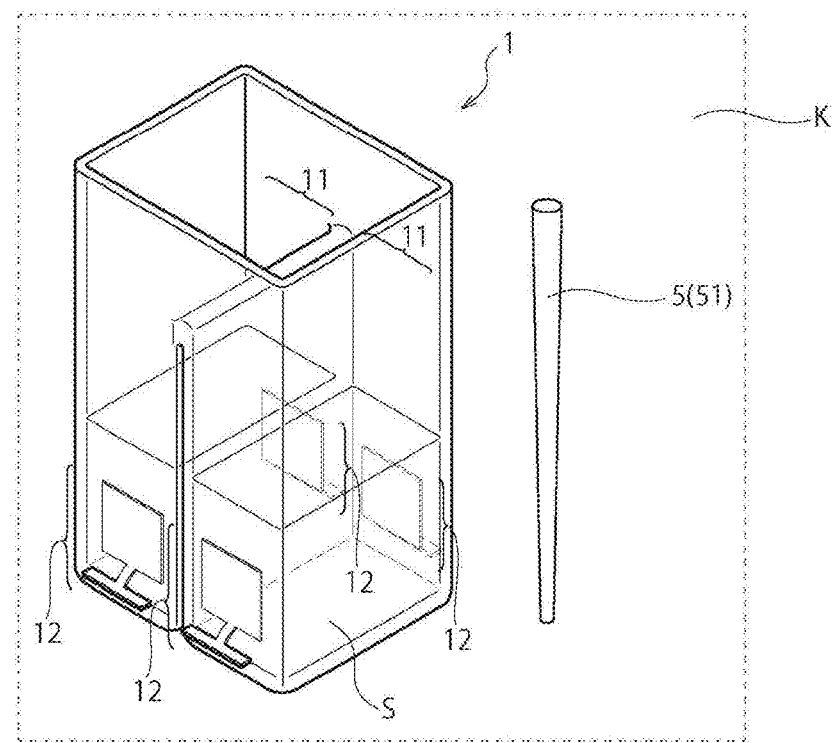
FIG. 15 is a schematic diagram schematically illustrating a first embodiment according to the present technology of an electrical measuring kit K.

FIG. 15 is a schematic diagram schematically illustrating a first embodiment of an electrical measuring kit K according to an embodiment of the present technology. In this embodiment, the previously-described electrical measuring cartridge 1 according to the first embodiment is used. The electrical measuring kit K according to the embodiment of the present technology roughly includes at least the previously-described electrical measuring cartridge 1, and a biological sample introducing member 5. It is noted that the electrical measuring cartridge 1 is similar to that previously described, and therefore description thereof is omitted here.

(1) Biological Sample Introducing Member 5

The biological sample introducing member 5 is a member configured to introduce the biological sample S into the biological sample holding section 11. An example thereof may include a tip 51 having a pipette shape, as illustrated in a first embodiment of FIG. 15. More specifically, a suction mechanism (for example, a pipetter) is disposed to the previously-described electrical measuring apparatus 10, and the tip 51 is attached to the suction mechanism, thereby enabling the biological sample S to be introduced.

The biological sample introducing member 5 according to the embodiment of the present technology is not limited to the tip 51 having a pipette shape illustrated as an example in FIG. 15, and may be freely selected depending on the type of the biological sample S, the measurement method, the electrical measuring apparatus to be used, and the like, as long as it is the whole or a portion of a tool with which the biological sample S can be introduced into the biological sample holding section 11. Another example thereof may include an injection needle, other than the tip 51 having a pipette shape.

The biological sample introducing member 5 may be configured as being disposable, in a similar manner to the electrical measuring cartridge 1. When the biological sample introducing member 5 is configured as being disposable, time and labor such as washing of a tool used for the introduction of a biological sample can be saved, thus achieving the improvement of user's convenience and the efficient measurement of electrical properties. Also, measurement error due to another biological sample S remained in the tool used for the introduction of a biological sample can be inhibited from occurring, thus also realizing the improvement of measurement accuracy during electrical measurement.

4. Electrical Measuring Method

The electrical measuring cartridge 1 according to the embodiment of the present technology may be appropriately used to measure the electrical properties of the biological sample S. The electrical properties that can be measured through an electrical measuring method according to the embodiment of the present technology are not particularly limited but may be freely measured according to the kind of the biological sample S, which is the measurement target, or physical properties to be analyzed. For example, permittivity, impedance, or the like, can be measured.

Using the electrical measuring method according to the embodiment of the present technology, for example, when the blood is to be measured as the biological sample S, a blood coagulation situation or a blood sedimentation situation can be analyzed from the measurement value of the permittivity or impedance. As a more specific example, for example, a parameter showing characteristics from a plurality of permittivity and/or impedance measurement values received during the analysis period can be derived, and the blood coagulation situation or the blood sedimentation situation can be analyzed based on comparison of the parameter with a reference value that determines a reference of acceleration of blood coagulability or progress of a blood sedimentation process.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An electrical measuring cartridge of a biological sample, the electrical measuring cartridge including at least:
  a plurality of biological sample holding sections each being configured to contain the biological sample; and
  a pair of electrical conductive sections fixed to each of the biological sample holding sections.

(2) The electrical measuring cartridge according to (1), wherein the biological sample holding sections and the electrical conductive sections are integrally molded in a state where the electrical conductive sections are partly embedded in the biological sample holding sections.

(3) The electrical measuring cartridge according to (1) or (2), wherein the biological sample holding sections are made of resin.

(4) The electrical measuring cartridge according to (3), wherein the electrical conductive sections are insert molded and integrated to the biological sample holding sections.

(5) The electrical measuring cartridge according to any one of (1) to (4), wherein the respective electrical conductive sections fixed to the at least two or more biological sample holding sections are aligned along an identical plane of the cartridge.

(6) The electrical measuring cartridge according to any one of (1) to (5), wherein the respective electrical conductive sections fixed to the at least two or more biological sample holding sections are molded by being molded in a state of having linkage sections to which portions of the electrical conductive sections are linked, and then cutting off the linkage sections.

(7) The electrical measuring cartridge according to (6), wherein the cutting-off is performed after the electrical conductive sections are integrally molded to the biological sample holding sections.

(8) The electrical measuring cartridge according to any one of (1) to (7),
  wherein each of the electrical conductive sections includes at least:
    an electrode section that comes into contact with the biological sample during measurement; and
    a connection section configured to electrically connect to an external circuit.

(9) The electrical measuring cartridge according to (8), wherein the electrode sections are partly used as a common electrode.

(10) The electrical measuring cartridge according to any one of (1) to (9), wherein a reagent is enclosed in a part of the biological sample holding sections.

(11) The electrical measuring cartridge according to any one of (1) to (10), wherein the biological sample is liquid.

(12) The electrical measuring cartridge according to any one of (1) to (11), wherein the biological sample contains a blood component.

(13) An electrical measuring apparatus including at least:
  a cartridge insertion section into which an electrical measuring cartridge of a biological sample is inserted, the electrical measuring cartridge including at least
    a plurality of biological sample holding sections each being configured to contain the biological sample, and
    a pair of electrical conductive sections fixed to each of the biological sample holding sections;
  an application unit that applies a voltage to the electrical conductive sections; and
  a measurement unit that measures an electrical property of the sample.

(14) An electrical measuring method of a biological sample, the method including:
  measuring an electrical property of the biological sample using an electrical measuring cartridge, the electrical measuring cartridge including at least
    a plurality of biological sample holding sections each being configured to contain the biological sample; and
    a pair of electrical conductive sections fixed to each of the biological sample holding sections.

What is claimed is:

1. An electrical measuring cartridge for analysis of a biological sample, the electrical measuring cartridge comprising at least:
  a plurality of biological sample holding sections each being configured to contain the biological sample;
  a respective pair of electrical conductive sections respectively fixed to each of the biological sample holding sections, one electrical conductive section in the pair of electrical conductive sections being respectively fixed to one side of a biological sample holding section and a second electrical conductive section in the pair of electrical conductive sections being respectively fixed to an opposite side of a biological sample holding section; and
  a plurality of closing sections respectively attached to and configured to be nested inside each biological sample holding section in the plurality of biological sample holding sections to separate a sealed portion of each biological sample holding section from each respective pair of electrical conductive sections.

2. The electrical measuring cartridge according to claim 1, wherein the biological sample holding sections and the electrical conductive sections are integrally molded in a state where the electrical conductive sections are partly embedded in the biological sample holding sections.

3. The electrical measuring cartridge according to claim 1, wherein the biological sample holding sections are made of resin.

4. The electrical measuring cartridge according to claim 3, wherein the electrical conductive sections are insert molded and integrated to the biological sample holding sections.

5. The electrical measuring cartridge according to claim 1, wherein the respective electrical conductive sections fixed to the plurality of biological sample holding sections are aligned along an identical plane of the cartridge.

6. The electrical measuring cartridge according to claim 1, wherein the respective electrical conductive sections fixed to the plurality of biological sample holding sections are molded by being molded in a state of having linkage sections to which portions of the electrical conductive sections are linked, and then cutting off the linkage sections.

7. The electrical measuring cartridge according to claim 1, wherein each of the electrical conductive sections comprises at least:
   an electrode section that comes into contact with the biological sample during measurement; and
   a connection section configured to electrically connect to an external circuit.

8. The electrical measuring cartridge according to claim 7, wherein the electrode sections partly comprise a common electrode.

9. The electrical measuring cartridge according to claim 1, wherein a reagent is enclosed in a part of the biological sample holding sections.

10. The electrical measuring cartridge according to claim 1, wherein the biological sample is liquid.

11. The electrical measuring cartridge according to claim 1, wherein the biological sample contains a blood component.

12. An electrical measuring apparatus comprising at least:
   a cartridge insertion section into which an electrical measuring cartridge for analysis of a biological sample is inserted, the electrical measuring cartridge including at least
      a plurality of biological sample holding sections each being configured to contain the biological sample,
      a respective pair of electrical conductive sections respectively fixed to each of the biological sample holding sections, one electrical conductive section in the pair of electrical conductive sections being respectively fixed to one side of a biological sample holding section and a second electrical conductive section in the pair of electrical conductive sections being respectively fixed to an opposite side of a biological sample holding section; and
   a plurality of closing sections respectively attached to and configured to be nested inside each biological sample holding section in the plurality of biological sample holding sections to separate a sealed portion of each biological sample holding section from each respective pair of electrical conductive sections;
   an application unit that applies a voltage to the electrical conductive sections; and
   a measurement unit that measures an electrical property of the sample.

13. An electrical measuring method for analysis of a biological sample, the method comprising:
   measuring an electrical property of the biological sample using an electrical measuring cartridge, the electrical measuring cartridge including at least
      a plurality of biological sample holding sections each being configured to contain the biological sample; and
      a respective pair of electrical conductive sections respectively fixed to each of the biological sample holding sections, one electrical conductive section in the pair of electrical conductive sections being respectively fixed to one side of a biological sample holding section and a second electrical conductive section in the pair of electrical conductive sections being respectively fixed to an opposite side of a biological sample holding section; and
   a plurality of closing sections respectively attached to and configured to be nested inside each biological sample holding section to separate a sealed portion of each biological sample holding section in the plurality of biological sample holding sections from each respective pair of electrical conductive sections.

* * * * *